United States Patent
Wang et al.

(10) Patent No.: US 10,737,250 B2
(45) Date of Patent: Aug. 11, 2020

(54) PDIN ALLOY CATALYST, METHOD FOR MANUFACTURING PDIN ALLOY CATALYST AND APPLICATION THEREOF

(71) Applicants: ZHEJIANG NHU COMPANY LTD., Shaoxing (CN); ZHEJIANG UNIVERSITY, Hangzhou (CN); SHANDONG NHU PHARMACEUTICAL CO., LTD., Weifang (CN); SHANDONG NHU VITAMIN CO., LTD., Weifang (CN)

(72) Inventors: Yong Wang, Hangzhou (CN); Lili Yu, Shaoxing (CN); Xiao Ma, Weifang (CN); Jianyong Mao, Weifang (CN); Zhe Wang, Hangzhou (CN); Shanjun Mao, Hangzhou (CN); Jianqing Li, Weifang (CN); Gang Chen, Hangzhou (CN); Haoran Li, Hangzhou (CN); Zhirong Chen, Hangzhou (CN)

(73) Assignees: ZHEJIANG NHU COMPANY LTD., Shaoxing (CN); ZHEJIANG UNIVERSITY, Hangzhou (CN); SHANDONG NHU PHARMACEUTICAL CO., LTD., Weifang (CN); SHANDONG NHU VITAMIN CO., LTD., Weifang (CN)

( * ) Notice: Subject to any disclaimer, the term of this patent is extended or adjusted under 35 U.S.C. 154(b) by 0 days.

(21) Appl. No.: 16/558,125

(22) Filed: Sep. 1, 2019

(65) Prior Publication Data

US 2020/0070132 A1    Mar. 5, 2020

Related U.S. Application Data

(63) Continuation of application No. PCT/CN2019/070893, filed on Jan. 8, 2019.

(30) Foreign Application Priority Data

Aug. 31, 2018    (CN) .......................... 2018 1 1010568

(51) Int. Cl.
| | | |
|---|---|---|
| B01J 27/24 | (2006.01) | |
| C07C 29/17 | (2006.01) | |
| B01J 35/00 | (2006.01) | |
| B01J 37/18 | (2006.01) | |
| B01J 37/08 | (2006.01) | |
| B01J 37/00 | (2006.01) | |
| B01J 37/03 | (2006.01) | |
| B01J 23/62 | (2006.01) | |
| B01J 35/10 | (2006.01) | |

(52) U.S. Cl.
CPC ............... *B01J 27/24* (2013.01); *B01J 23/62* (2013.01); *B01J 35/0066* (2013.01); *B01J 35/0093* (2013.01); *B01J 35/1019* (2013.01); *B01J 37/0018* (2013.01); *B01J 37/035* (2013.01); *B01J 37/086* (2013.01); *B01J 37/088* (2013.01); *B01J 37/18* (2013.01); *C07C 29/17* (2013.01)

(58) Field of Classification Search
USPC .......................................................... 568/909
See application file for complete search history.

(56) References Cited

U.S. PATENT DOCUMENTS

2012/0207667 A1* 8/2012 Men .................... B01J 35/1019
                                                                 423/648.1

FOREIGN PATENT DOCUMENTS

| CN | 106345508 A | 1/2017 |
| CN | 106622327 A | 5/2017 |
| CN | 106732559 A | 5/2017 |

OTHER PUBLICATIONS

Li at al. Catal. Sci. Technol., 2016, 6, 3670-3693.*

* cited by examiner

*Primary Examiner* — Ana Z Muresan (57) ABSTRACT

The present disclosure provides a PdIn alloy catalyst including a carrier and Pd metal particles supported by the carrier, the carrier is a nitrogen-doped porous carbon composite material having a plurality of passages, Pd metal particles are distributed in the plurality of passages, the nitrogen-doped porous carbon composite material includes a nitrogen-doped porous carbon material, a plurality of indium oxide particles, and In metal particles. The In metal particles are exposed through the plurality of passages, the plurality of indium oxide particles are uniformly distributed in the nitrogen-doped porous carbon material, and In atoms of the In metal particles migrated to surfaces of Pd particles selectively occupy edge and corner positions of metal lattice of Pd metal particles. The present disclosure further provides a method for manufacturing the PdIn alloy catalyst and application thereof.

9 Claims, 5 Drawing Sheets

PDIN ALLOY CATALYST, METHOD FOR MANUFACTURING PDIN ALLOY CATALYST AND APPLICATION THEREOF

CROSS-REFERENCE TO RELATED APPLICATIONS

This application is a continuation of PCT patent application PCT/CN2019/070893 filed on Jan. 8, 2019, which claims all benefits accruing under 35 U.S.C. § 119 from China Patent Application No. 201811010568.6, filed on Aug. 31, 2018, in the China National Intellectual Property Administration, the content of which is hereby incorporated by reference.

TECHNICAL FIELD

The present disclosure relates to the technical field of a catalyst, in particular, to a PdIn alloy catalyst, method for manufacturing a PdIn alloy catalyst and application thereof.

BACKGROUND

Vitamins are a kind of trace organic substance that must be obtained from foods to maintain normal physiological functions of living organisms. They play an important role in the growth, metabolism and development of human body. Synthesis of vitamins in vitamin production has an increased proportion year by year, and a selective hydrogenation of alkynol substances is one of the most important reactions in vitamin production. Supported Pd catalysts are commonly used in these reactions. At present, a catalyst for the hydrogenation reaction of the alkynol substances in industrial production is mainly a Lindlar catalyst. However, the Lindlar catalyst still has many disadvantages such as high toxicity, poor stability of water phase and insufficient selectivity. It is urgent to develop a more efficient and stable catalyst for selective hydrogenation of the alkynol substances.

Recently, Pd-based alloy catalysts have attracted extensive attention in the field of hydrogenation of the alkynol substances, especially Pd-based alloy catalysts obtained by high-temperature hydrogen reduction with a reducible oxide as a support. However, such catalysts generally have problems such as low specific surface area, and a formation of these alloys will reduce Pd sites exposed on its surface, thereby reducing catalytic activity. The carbon material has a large specific surface area, is easy to control and an ideal catalyst carrier. Compared with an ordinary carbon material, nitrogen-doped carbon material has some unique advantages. For embodiment, a doping of nitrogen can change a local electronic structure of carbon materials, which is beneficial to a dispersion of noble metal nanoparticles; it will enhance an activity and stability of the catalyst through a mutual interaction between nitrogen and metals. However, how to combine the advantages of the two carriers and prepare a metal oxide and nitrogen-doped porous carbon alloy composite catalyst loaded Pd in high dispersion with unique performance still has enormous challenges. Recently, Wang et al. (J. Catal. 2017, 350, 13-20) developed a PdZn/CN coated ZnO catalyst based on a theory that Pd particles on edge and corner positions can cause an excess-hydrogenation of the alkynol. Zn poisons the edge and corner positions of Pd particles, but this poisoning is not selective, and Zn atom also occupies a flat position, causing a decrease of catalyst activity.

SUMMARY

The present disclosure provides a PdIn alloy catalyst, a method for manufacturing the PdIn alloy catalyst and application thereof. Edge and corner positions of metal lattice of Pd metal particles in the PdIn alloy catalyst can be occupied by In atoms of In metal particles to achieve selective poisoning and thus the PdIn alloy catalyst has an excellent catalytic property.

The present disclosure provides a PdIn alloy catalyst including a carrier and Pd metal particles supported by the carrier, the carrier is a nitrogen-doped porous carbon composite material having a plurality of passages, Pd metal particles are distributed in the plurality of passages, the nitrogen-doped porous carbon composite material includes a nitrogen-doped porous carbon material, a plurality of indium oxide particles, and In metal particles. The In metal particles are partially exposed through the plurality of passages, the plurality of indium oxide particles are uniformly distributed in the nitrogen-doped porous carbon material, and In atoms of the In metal particles migrated to surfaces of Pd particles selectively occupy edge and corner positions of metal lattice of Pd metal particles.

The Pd metal particles have a dispersity of 70% to 95% in the nitrogen-doped porous carbon composite material.

A weight percentage of the Pd metal particles in the PdIn alloy catalyst is in a range of 0.1% to 10%, a weight percentage of a sum of the plurality of indium oxide particles and the In metal particles in the PdIn alloy catalyst is in a range of 2% to 30%, a weight percentage of the nitrogen-doped porous carbon composite material in the PdIn alloy catalyst is in a range of 60% to 97.9%, wherein a weight percentage of nitrogen element in the nitrogen-doped porous carbon composite material is in a range of 0.5% to 15%.

A method for manufacturing a PdIn alloy catalyst can include the following steps:

1) providing a nitrogen-doped porous carbon composite material having a plurality of passages, wherein the nitrogen-doped porous carbon composite material includes a nitrogen-doped porous carbon material and a plurality of indium oxide particles, the plurality of indium oxide particles are uniformly distributed in the nitrogen-doped porous carbon material, and a part of the plurality of indium oxide particles are exposed through the plurality of passages;

2) immersing the nitrogen-doped porous carbon composite material in a Pd metal precursor solution;

3) treating the nitrogen-doped porous carbon composite material by a first calcination, in order to convert a Pd metal precursor in the Pd metal precursor solution into Pd metal particles, which are distributed in the plurality of passages; and 4) undergoing a hydrogen reduction on the nitrogen-doped porous carbon composite material, wherein in a process of hydrogen reduction, the part of the plurality of indium oxide particles exposed through the plurality of passages are reduced to In metal particles, and In atoms of the In metal particles migrated to surfaces of Pd particles selectively occupy edge and corner positions of metal lattice of Pd metal particles, in order to combine with Pd metal particles.

The nitrogen-doped porous carbon composite material is prepared by the following steps:

a) dissolving an indium nitrate in water to obtain a premix;

b) sequentially adding a nitrogen-containing biomass and a pore-forming agent to the premix, such that the indium nitrate reacts with the pore-forming agent to obtain a mixture containing a metal precipitate, wherein the pore-forming agent is at least one selected from a group of ammonium bicarbonate, ammonium carbonate, ammonium oxalate, ammonium hydrogen oxalate, and oxalic acid, a molar ratio of the indium nitrate to the pore-forming agent is 1:1 to 1:20; and c) treating the mixture by a second calcination at 500 degree centigrades to 1200 degree centigrades under an inert atmosphere to obtain the nitrogen-doped porous carbon composite material having the plurality of passages.

The Pd metal precursor in the Pd metal precursor solution is at least one selected from a group of $PdCl_2$, $H_2PdCl_4$, $Pd(NO_3)_2$, and $Pd(NH_3)_4(NO_3)_2$.

In the first calcination of step 3), a calcination temperature is in a range of 200 degree centigrades to 500 degree centigrades, a heating rate is in a range of 1 degree centigrade per minute to 20 degree centigrades per minute, the time is in a range of 1 minute to 240 minutes; in the hydrogen reduction, a reduction temperature is in a range of 50 degree centigrades to 500 degree centigrades, a heating rate is in a range of 1 degree centigrade per minute to 20 degree centigrades per minute, the time is in a range of 1 minute to 360 minutes, and a flow rate of hydrogen gas is in a range of 20 milliliters per minute to 200 milliliters per minute.

In step b), the nitrogen-containing biomass is at least one selected from a group of bamboo, chitin, carboxymethyl chitin, chitosan, carboxymethyl chitosan, and glucosamine hydrochloride.

In step b), a mass ratio of the indium nitrate to the nitrogen-containing biomass is 0.05:1 to 2:1.

In the step c), a calcination time during the second calcination is in a range of 0.1 hour to 5 hours.

The PdIn alloy catalyst and the method for manufacturing the same have the following advantages:

In atoms of the In metal particles selectively occupying the edge and corner positions of metal lattice of the Pd metal particles means that the indium oxide partially exposed through the plurality of passages can be reduced to form In metal particles, which will migrate to surfaces of Pd particles. In atoms preferentially occupy the edge and corner positions of metal lattice of the Pd metal particles, which are with lower coordination number and relatively unsaturated. Such that the Pd metal particles can be selectivity poisoned, resulting in a unique catalytic property of the PdIn alloy catalyst in the selective hydrogenation.

In a process of preparing the nitrogen-doped porous carbon composite material, on the one hand, a carbonate ion or a hydrogen carbonate ion in the pore-forming agent can react with an Indium ion in the indium nitrate to obtain the metal precipitate uniformly distributed; on the other hand, the pore-forming agent and metal precipitate can be decomposed during the subsequent calcination, and a gas can be generated, forming the plurality of passages in the nitrogen-doped porous carbon material. During the process of calcination, the metal precipitate can be decomposed to form nanoscale indium oxide. Finally the indium oxide can be uniformly distributed in the nitrogen-doped porous carbon material, and a part of the surface of the indium oxide can be exposed through the plurality of passages. It should be noted that in the reaction of the pore-forming agent and the metal source, the pore-forming agent does not need to be excessive relative to the metal source, and even if the carbonate or oxalate in the pore-forming agent is transferred into the metal precipitate, the metal precipitate can be also decomposed and the gas can be generated in order to form a pore-forming effect.

In addition, since indium oxide is dispersed in the form of nanoparticles on the carbon material, that is, the In metal particles formed in the plurality of passages is also relatively uniform, the Pd metal particles can be also highly dispersed in the nitrogen-doped porous carbon material, avoiding Pd metal aggregated during the reduction process. The manufacturing method is simple and easy to industrialize.

In atoms in the PdIn alloy catalyst selectively poison the edge and corner positions of metal lattice of the Pd metal particles, and thus is applicable to selective hydrogenation of the alkynol. In addition, the PdIn alloy catalyst has a large specific surface area, which is also beneficial for adsorption of a reactant and has high catalytic activity.

The present disclosure also provides an application of a PdIn alloy catalyst as a catalyst in a catalytic hydrogenation reaction in a selective hydrogenation reaction of an alkyne alcohol.

Preferably, the alkynol is at least one selected from a group of 2-methyl-3-butyn-2-ol, 3,7-dimethyl-1-octyn-3-ol, 3,7-dimethyl-6-octene-1-yne-3-ol, 3,7,11-trimethyl-1-dodecyn-3-ol, 3,7,11-trimethyl-6-dodecen-1-yne-3-ol, 3,7,11-trimethyl-6,10-dodecanediene-1-yne-3-ol, 3,7,11,15-tetramethyl-1-hexadecyne-3-ol, 3-methyl-1-(2,6,6-trimethyl-1-cyclohexene-1-yl)-1-penten-4-yne-3-ol, and 3,6-dimethyl-8-(2,6,6-trimethyl-1-cyclohexen-1-yl)-2,7-octadien-4-yne-1,6-diol.

Since the structure of the Pd metal particles in the PdIn alloy catalyst is stable, the PdIn alloy catalyst can be reused multiple times.

DETAILED DESCRIPTION

The technical solutions of the embodiments of the present disclosure are clearly and completely described below. It is obvious that the described embodiments are only a part and not all of the embodiments of the present disclosure. All other embodiments obtained by one skilled in the art based on the embodiments of the present disclosure without any creative efforts are within the scope of the present disclosure.

The present disclosure provides a method for manufacturing a PdIn alloy catalyst. The method includes the following steps:

S1, providing a nitrogen-doped porous carbon composite material having a plurality of passages, wherein the nitrogen-doped porous carbon composite material comprises a nitrogen-doped porous carbon material and a plurality of indium oxide particles, the plurality of indium oxide particles are uniformly distributed in the nitrogen-doped porous carbon material, and a part of the plurality of indium oxide particles are exposed through the plurality of passages;

S2, immersing the nitrogen-doped porous carbon composite material in a Pd metal precursor solution;

S3, treating the nitrogen-doped porous carbon composite material by a first calcination, in order to convert a Pd metal precursor in the Pd metal precursor solution into a plurality of Pd metal particles, which is distributed in the plurality of passages;

S4, undergoing a hydrogen reduction on the nitrogen-doped porous carbon composite material, wherein in a process of hydrogen reduction, the part of the plurality of indium oxide particles exposed through the plurality of passages are reduced to In metal particles, and In atoms of the In metal particles migrated to surfaces of Pd particles selectively occupy edge and corner positions of metal lattice of the plurality of Pd metal particles, in order to combine with the plurality of Pd metal particles.

In the step S1, the nitrogen-doped porous carbon composite material is prepared by the following steps:

a) dissolving an indium nitrate in water to obtain a premix;

b) sequentially adding a nitrogen-containing biomass and a pore-forming agent to the premix, such that the indium nitrate reacts with the pore-forming agent to obtain a mixture containing a metal precipitate, wherein the pore-forming agent is at least one selected from a group of ammonium bicarbonate, ammonium carbonate, ammonium oxalate, ammonium hydrogen oxalate, and oxalic acid, a molar ratio of the indium nitrate to the pore-forming agent is 1:1 to 1:20;

c) treating the mixture by a second calcination at 500 degree centigrades to 1200 degree centigrades under an inert atmosphere to obtain the nitrogen-doped porous carbon composite material having the plurality of passages.

A ratio of the indium nitrate to the water is not limited. Preferably, the ratio of a mass of the indium nitrate to a volume of the water is 1 g:100 mL to 10 g:100 mL.

The nitrogen-containing biomass is at least one selected from a group of bamboo, chitin, carboxymethyl chitin, chitosan, carboxymethyl chitosan, and glucosamine hydrochloride. The nitrogen-containing biomass includes a nitrogen element and a carbon element as a nitrogen source and a carbon source, respectively. The nitrogen-containing biomass is insoluble in the water.

The indium nitrate can react with a part of the pore-forming agent to form the metal precipitate. The metal precipitate is formed by carbonate ions and metal ions. An excess part of the pore-forming agent decomposes during subsequent calcination to form a gas which plays a role of forming pore and results in the plurality of passages in the nitrogen-doped porous carbon material. The mass ratio of the indium nitrate to the nitrogen-containing biomass can be 0.05:1 to 2:1. Preferably, the mass ratio of the indium nitrate to the nitrogen-containing biomass is 0.5:1 to 2:1. There can be a continuous stirring for 0.1 hour to 10 hours during the reaction. The obtained mixture is actually a suspension, in which the metal precipitate formed and the nitrogen-containing biomass are insoluble in a solvent, but are evenly distributed in the mixture. So, the mixture is a suspension.

It will be understood that the mixture is dried before the second calcination, and a process of drying can be as following: drying at a temperature with a range of 60 degree centigrades to 180 degree centigrades.

The time of the second calcination can be in a range of 0.1 hour to 5 hours. A process of the second calcination is as follows: the temperature is raised to a range of 500 degree centifrades to 1200 degree centigrades at a heating rate of 2 degree centigrades per minute to 30 degree centigrades per minute, the mixture is calcined at the temperature of 500 degree centigrades to 1200 degree centigrades for 0.1 hour to 5 hours and finally naturally cooled to a room temperature. Preferably, the temperature of the second calcination is from 600 degree centigrades to 900 degree centigrades.

In step S2, a loading amount (i.e., mass fraction) of the Pd metal particles in the PdIn alloy catalyst can be regulated, which is not limited. For embodiment, the loading amount of the Pd metal particles in the PdIn alloy catalyst can be adjusted by the quality or a molar amount of the Pd metal precursor in the Pd metal precursor solution.

The method for forming Pd metal particles in the plurality of passages of the nitrogen-doped porous carbon composite material can be as follows: immersing the nitrogen-doped porous carbon composite material in the Pd metal precursor solution; and subsequently treating the nitrogen-doped porous carbon composite material by the first calcination and hydrogen reduction in order. Pd metal particles can be formed in the plurality of passages of the nitrogen-doped porous carbon composite. In the first calcination, the temperature is in a range of 200 degree centigrades to 500 degree centigrades, the heating rate is in a range of 1 degree centigrade per minute to 20 degree centigrades per minute, and the time is in a range of 1 minute to 240 minutes. In the hydrogen reduction, the temperature is in a range of 150 degree centigrades to 500 degree centigrade, the heating rate is in a range of 1 degree centigrade per minute to 20 degree centigrades per minute, the time is in a range of 1 minute to 360 minutes, and a flow rate of hydrogen gas is in a range of 20 milliliters per minute to 200 milliliters per minute. Preferably, in the first calcination, the temperature is in a range of 300 degree centigrades to 500 degree centigrades, the heating rate is in a range of 5 degree centigrades per minute to 10 degree centigrades per minute, and the time is in a range of 60 minutes to 120 minutes; in the hydrogen reduction, the temperature is in a range of 200 degree centigrades to 400 degree centigrade, the heating rate is in a range of 5 degree centigrades per minute to 10 degree centigrades per minute, the time is in a range of 60 minutes to 180 minutes, and the flow rate of hydrogen gas is in a range of 40 milliliters per minute to 100 milliliters per minute.

The Pd metal precursor in the Pd metal precursor solution can be at least one selected from a group of $PdCl_2$, $H_2PdCl_4$, $Pd(NO_3)_2$, and $Pd(NH_3)_4(NO_3)_2$.

The present disclosure further provides a PdIn alloy catalyst including a carrier and Pd metal particles supported by the carrier. The carrier can be a nitrogen-doped porous carbon composite material having a plurality of passages. Pd metal particles can be distributed in the plurality of passages. The nitrogen-doped porous carbon composite material includes a nitrogen-doped porous carbon material, a plurality of indium oxide particles, and In metal particles. The In metal particles can be partially exposed through the plurality of passages. The plurality of indium oxide particles are uniformly distributed in the nitrogen-doped porous carbon material. And In atoms of the In metal particles selectively occupy edge and corner positions of metal lattice of the Pd metal particles. That is, only an exposed portion of indium oxide ($In_2O_3$) is reduced to form the In metal, and a unexposed portion of indium oxide is still not reduced.

The Pd metal particles have a dispersity of 70% to 95% in the nitrogen-doped porous carbon composite material. Preferably, the Pd metal particles have a dispersity of 70% to 80% in the nitrogen-doped porous carbon composite material.

A weight percentage of the Pd metal particles in the PdIn alloy catalyst is in a range of 0.1% to 10%. A weight percentage of a sum of the plurality of indium oxide particles and the In metal in the PdIn alloy catalyst is in a range of 2% to 30%. A weight percentage of the nitrogen-doped porous carbon composite material in the PdIn alloy catalyst is in a range of 60% to 97.9%. And a weight percentage of nitrogen element in the nitrogen-doped porous carbon composite material is in a range of 0.5% to 15%.

Figure 5:
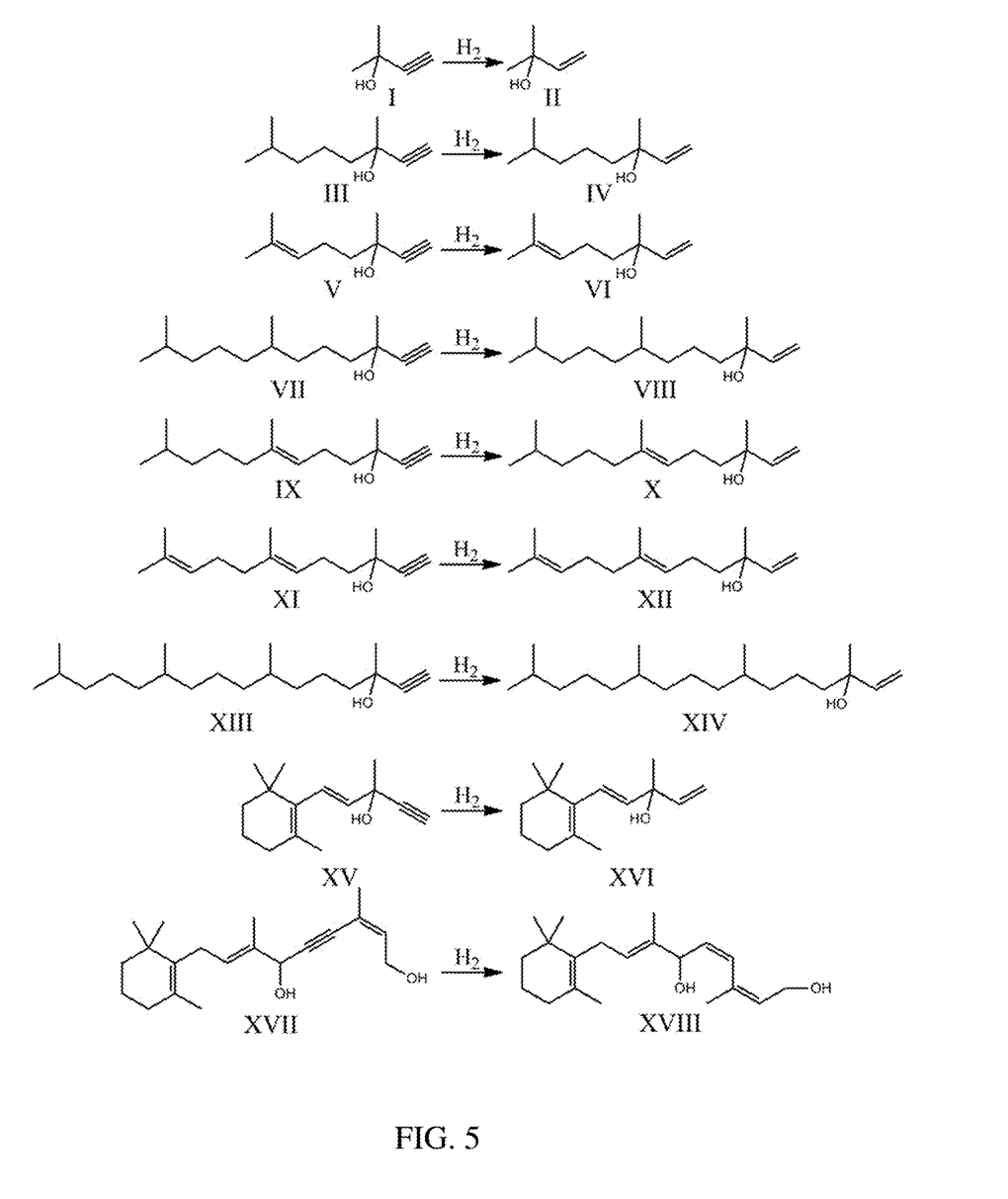
FIG. 5 is a schematic view showing processes of selective hydrogenations using PdIn alloy catalysts in the present disclosure.

Referring to FIG. 5, the present disclosure also provides an application of the PdIn alloy catalyst in a catalytic hydrogenation reaction. The PdIn alloy catalyst can act as a catalyst in a selective hydrogenation reaction of an alkynol. And the alkynol is at least one selected from a group of 2-methyl-3-butyn-2-ol, 3,7-dimethyl-1-octyn-3-ol, 3,7-dimethyl-6-octene-1-yne-3-ol, 3,7,11-trimethyl-1-dodecyn-3-ol, 3,7,11-trimethyl-6-dodecen-1-yne-3-ol, 3,7,11-trimethyl-6,10-dodecanediene-1-yne-3-ol, 3,7,11,15-tetramethyl-1-hexadecyne-3-ol, 3-methyl-1-(2,6,6-trimethyl-1-cyclohexene-1-yl)-1-penten-4-yne-3-ol, and 3,6-dimethyl-8-(2,6,6-trimethyl-1-cyclohexen-1-yl)-2,7-octadien-4-yne-1,6-diol.

The PdIn alloy catalyst of the present disclosure and its application will be further described below by multiple embodiments.

Embodiment 1

Approximately 1 g indium nitrate hydrate was weighed and dispersed in approximately 30 mL water. After the indium nitrate hydrate was dissolved, 3 g carboxymethyl chitin was added and stirred for about 1 hour. Then approximately 3 g ammonium bicarbonate was slowly added and stirred for about 1 hour to obtain a mixture. Then the temperature rose to about 80 degree centigrades while stirring until dry. Then, the mixture was transferred to a crucible and underwent a calcination process in a nitrogen furnace. The calcination process was as follows: heating to about 1000 degree centigrades at a heating rate of about 5 degree centigrades per minute, calcining at about 1000 degree centigrades for about 1 hour; then, naturally cooling to room temperature. The mixture calcined was ground to obtain a nitrogen-doped porous carbon composite.

Approximately 1 g nitrogen-doped porous carbon composite material was weighed and added to approximately 60 mL deionized water. Approximately 1 mL $PdCl_2$ solution with a molar concentration of about 10 mg/mL was slowly added dropwise, stirred at about 50 degree centigrades for about 12 h, and placed in an oven of about 70 degree centigrades for about 24 h. It was further calcined at about 200 degree centigrades for about 1 h in the air. Finally, after a hydrogen reduction at about 300 degree centigrades for about 1 h (wherein, a flow rate of hydrogen gas was about 50 milliliters per minute, heating rate was about 5 degree centigrade per minute), PdIn alloy catalyst was obtained. A theoretical loading amount (weight percentage) of Pd metal particles in the PdIn alloy catalyst was 0.6%.

An actual loading amount of Pd metal particles in the PdIn alloy catalyst was about 0.59% measured by atomic emission spectroscopy, which was approximately consistent with the theoretical load amount of Pd metal particles in the PdIn alloy catalyst.

Figure 1:
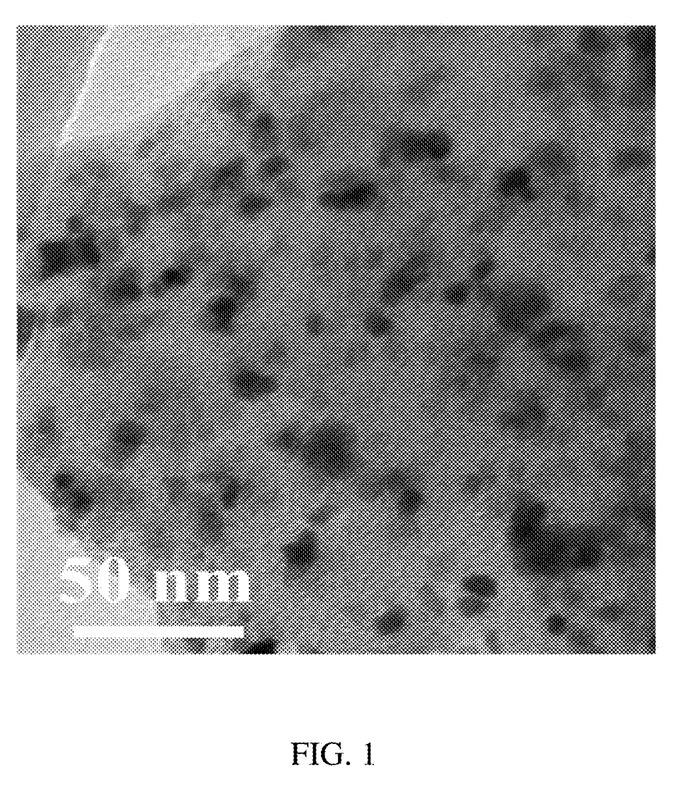
FIG. 1 is a scanning electron micrograph of a nitrogen-doped porous carbon composite material in embodiment 1.
Figure 2:
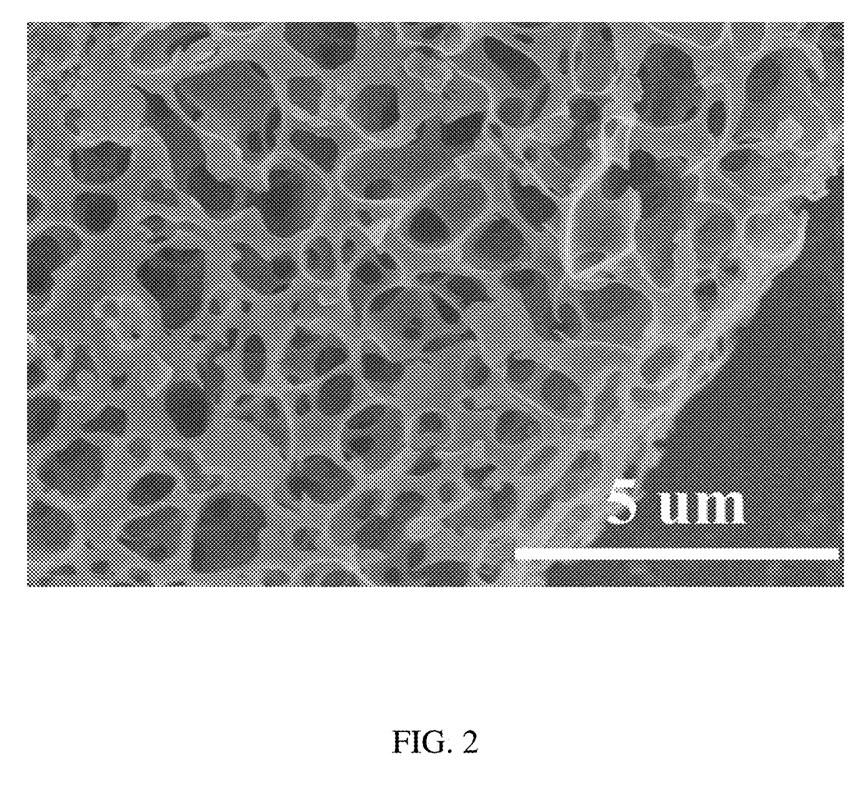
FIG. 2 is a transmission electron micrograph of a nitrogen-doped porous carbon composite material in embodiment 1.

The nitrogen-doped porous carbon composite material was measured by a scanning electron microscopy, and the result was shown in FIG. 1. Referring to FIG. 1, a plurality of pores and passages can be clearly observed. The nitrogen-doped porous carbon composite was measured by a transmission electron microscopy, and the result was shown in FIG. 2. Referring to FIG. 2, indium oxide was uniformly dispersed in the nitrogen-doped porous carbon composite.

Figure 3:
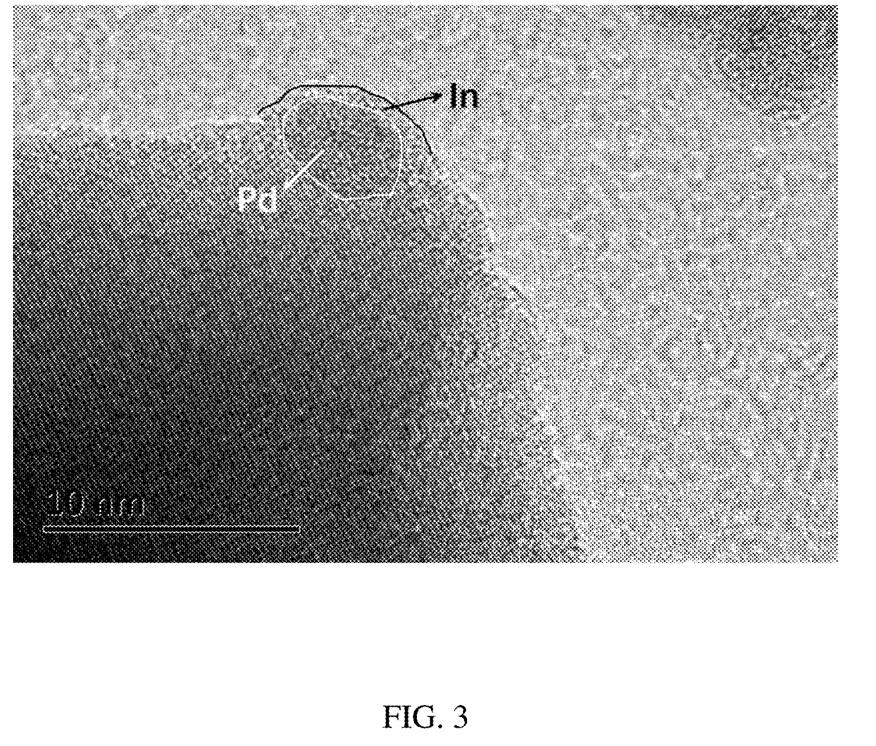
FIG. 3 is a transmission electron micrograph of a PdIn alloy catalyst in embodiment 1.

The PdIn alloy catalyst was measured by a high-rate transmission electron microscopy, and the result was shown in FIG. 3. Referring to FIG. 3, edge and corner positions of the Pd metal particles were partially occupied by In atoms of the In metal particles.

Figure 4:
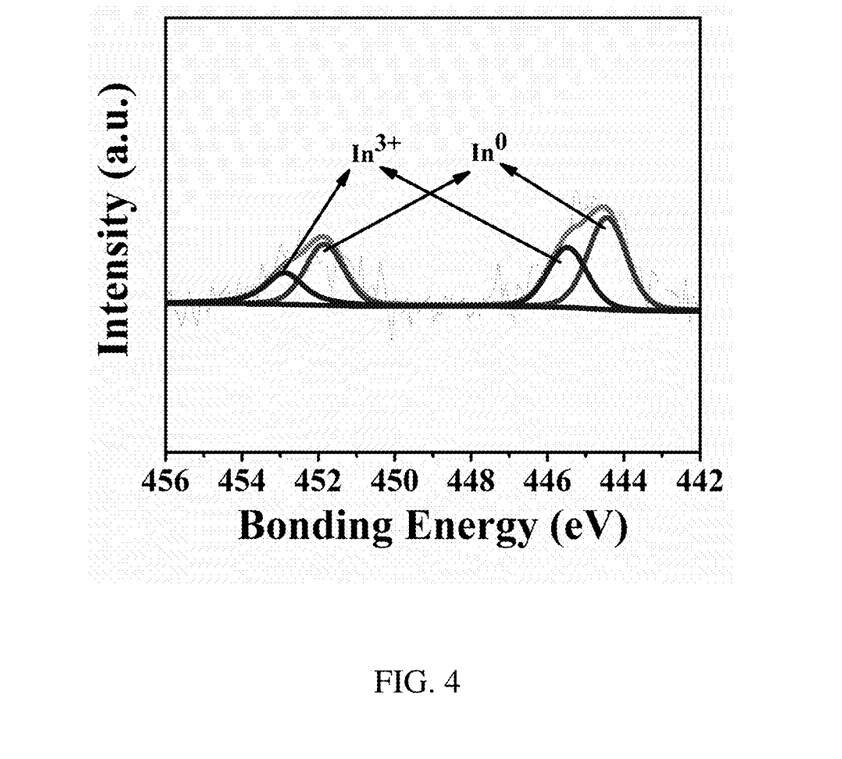
FIG. 4 is an X-ray photoelectron spectroscopy of a PdIn alloy catalyst in embodiment 1.

The PdIn alloy catalyst was measured by a X-ray photoelectron spectroscopy, and the result were shown in FIG. 4. Referring to FIG. 4, the PdIn alloy catalyst included $In^0$ in a metallic state.

Pd dispersion and specific surface area of the PdIn alloy catalyst were measured by CO titration method, wherein CO titration method is a carbon monoxide adsorption test for measuring Pd metal dispersion. The results were: the Pd dispersion of the PdIn alloy catalyst was about 73%, and the specific surface area of the PdIn alloy catalyst was about 113.7 $m^2\ g^{-1}$.

Embodiment 2

Approximately 1 g indium nitrate hydrate was weighed and dispersed in about 30 mL water. After the indium nitrate hydrate was dissolved, about 3 g carboxymethyl chitosan was added and stirred for about 1 hour. Then about 3 g ammonium bicarbonate was slowly add and stirred for about 1 hour to obtain a mixture. Then the temperature rose to about 80° degree centigrades while stirring until dry. Then, the mixture was transferred to a crucible and underwent a calcination process in a nitrogen furnace. The calcination process was as follows: heating to about 1000 degree centigrades at a heating rate of about 5 degree centigrades per minute, calcining at about 1000 degree centigrades for 1 hour; then, naturally cooling to room temperature. The mixture calcined was ground to obtain a nitrogen-doped porous carbon composite.

Approximately 1 g nitrogen-doped porous carbon composite material was weighed and added to about 60 mL deionized water. About 1 mL $PdCl_2$ solution with a molar concentration of about 10 mg/mL was slowly added dropwise, stirred at about 50 degree centigrades for about 12 h, and placed in an oven of about 70 degree centigrades for about 24 h. It was further calcined at about 200 degree centigrades for about 1 h in the air. Finally, after a hydrogen reduction at about 300 degree centigrades for about 1 h (wherein, a flow rate of hydrogen gas was about 50 milliliters per minute, heating rate was about 5 degree centigrade per minute), PdIn alloy catalyst was obtained.

The method of the PdIn alloy catalyst in Embodiment 2 was substantially the same as that of the PdIn alloy catalyst in Embodiment 1, except that the nitrogen-containing biomass was carboxymethyl chitosan.

Pd dispersion and specific surface area of the PdIn alloy catalyst were measured by CO titration method. The results were: the Pd dispersion of the PdIn alloy catalyst was about 77%, and the specific surface area of the PdIn alloy catalyst was about 126.6 $m^2\ g^{-1}$.

Referring to FIG. 5, the processes of the hydrogenation reaction in the following embodiments were showed.

Embodiment 3

The PdIn alloy catalyst catalyzes a selective hydrogenation of 2-methyl-3-butyn-2-ol (I) by following process.

Approximately 50 mg PdIn alloy catalyst obtained in Embodiment 1 was added to a 50 mL autoclave. Approximately 20 mmol 2-methyl-3-butyn-2-ol and about 5 mL ethanol were added. The reaction was taken under a hydrogen pressure of about 1 MPa, a reaction temperature of about 30 degree centigrade and reaction time of about 2 hours. A conversion of 2-methyl-3-butyn-2-ol (I) was about 100%, and a selectivity of 2-methyl-3-buten-2-ol (II) was about 98%.

Further, a comparative embodiment 1 and a comparative embodiment 2 were provided. The comparative embodiment 1 and the comparative embodiment 2 were respectively Pd/Al$_2$O$_3$ and Pd/ZnO catalysts prepared by a conventional impregnation method. A conversion and selectivity of the Pd/Al$_2$O$_3$ catalyst were about 100% and about 72%, respectively. A conversion and selectivity of the Pd/ZnO catalyst were about 15% and about 99%, respectively. Thus, the highly dispersed PdIn alloy catalyst in embodiment 1 has greatly improved the selectivity of the catalyst while maintaining the activity of the catalyst.

Embodiment 4

The PdIn alloy catalyst catalyzes a selective hydrogenation of 3,7-dimethyl-1-octyn-3-ol (III) by following process.

Approximately 50 mg PdIn alloy catalyst obtained in Embodiment 1 was added to a 50 mL autoclave. Approximately 20 mmol 3,7-dimethyl-1-octyn-3-ol (III) and about 5 mL ethanol were added. The reaction was taken under a hydrogen pressure of about 1 MPa, a reaction temperature of 30 degree centigrade and reaction time of about 2 hours. A conversion of 3,7-dimethyl-1-octyn-3-ol (III) was about 100%, and a selectivity of 3,7-dimethyl-1-octene-3-ol (IV) was about 98%.

Embodiment 5

The PdIn alloy catalyst catalyzes a selective hydrogenation of 3,7-dimethyl-6-octene-1-yn-3-ol (V) by following process.

Approximately 50 mg PdIn alloy catalyst obtained in Embodiment 1 was added to a 50 mL autoclave. About 20 mmol 3,7-Dimethyl-6-octene-1-yn-3-ol (V) and about 5 mL ethanol were added. The reaction was taken under a hydrogen pressure of 1 MPa, a reaction temperature of 30 degree centigrade and reaction time of 2 hours. A conversion of 3,7-Dimethyl-6-octene-1-yn-3-ol (V) was 100%, and a selectivity of 3,7-dimethyl-1,6-octadien-3-ol (VI) was 98%.

Embodiment 6

The PdIn alloy catalyst catalyzes a selective hydrogenation of 3,7,11-trimethyl-1-dodecyne-3-ol (VII) by following process.

Approximately 50 mg PdIn alloy catalyst obtained in Embodiment 1 was added to a 50 mL autoclave. Approximately 20 mmol 3,7,11-trimethyl-1-dodecyne-3-ol (VII) and about 5 mL ethanol were added. The reaction was taken under a hydrogen pressure of about 1 MPa, a reaction temperature of about 30 degree centigrade and reaction time of about 2 hours. A conversion of 3,7,11-trimethyl-1-dodecyne-3-ol (VII) was about 100%, and, and a selectivity of 3,7,11-trimethyl-1-dodecen-3-ol (VIII) was about 98%.

Embodiment 7

The PdIn alloy catalyst catalyzes a selective hydrogenation of 3,7,11-trimethyl-6-dodecen-1-yn-3-ol (IX) by following process.

Approximately 50 mg PdIn alloy catalyst obtained in Embodiment 1 was added to a 50 mL autoclave. Approximately 20 mmol 3,7,11-trimethyl-6-dodecen-1-yn-3-ol (IX) and about 5 mL ethanol were added. The reaction was taken under a hydrogen pressure of about 1 MPa, a reaction temperature of about 30 degree centigrade and reaction time of about 2 hours. A conversion of 3,7,11-trimethyl-6-dodecen-1-yn-3-ol (IX) was about 100%, and a selectivity of 3,7,11-trimethyl-1,6-dodecandien-3-ol (X) was about 98%.

Embodiment 8

The PdIn alloy catalyst catalyzes a selective hydrogenation of 3,7,11-trimethyl-6,10-dodecadien-1-yn-3-ol (XI) by following process.

Approximately 50 mg PdIn alloy catalyst obtained in Embodiment 1 was added to a 50 mL autoclave. Approximately 15 mmol 3,7,11-trimethyl-6,10-dodecadien-1-yn-3-ol (XI) and about 5 mL ethanol were added. The reaction was taken under a hydrogen pressure of about 1 MPa, a reaction temperature of about 30 degree centigrade and reaction time of about 2 hours. A conversion of 3,7,11-trimethyl-6,10-dodecadien-1-yn-3-ol (XI) was about 100%, and a selectivity of 3,7,11-trimethyl-1,6,10-dodecanetrien-3-ol (X) was about 98%.

Embodiment 9

The PdIn alloy catalyst catalyzes a selective hydrogenation of 3,7,11,15-tetramethyl-1-hexadecan-3-ol (XIII) by following process.

Approximately 50 mg PdIn alloy catalyst obtained in Embodiment 1 was added to a 50 mL autoclave. Approximately 20 mmol 3,7,11,15-tetramethyl-1-hexadecan-3-ol (XIII) and about 5 mL ethanol were added. The reaction was taken under a hydrogen pressure of about 1 MPa, a reaction temperature of about 30 degree centigrade and reaction time of about 2 hours. A conversion of 3,7,11,15-tetramethyl-1-hexadecan-3-ol (XIII) was about 100%, and a selectivity of 3,7,11,15-tetramethyl-1-hexadecen-3-ol (XIV) was about 98%.

Embodiment 10

The PdIn alloy catalyst catalyzes a selectivity hydrogenation of 3-methyl-1-(2,6,6-trimethyl-1-cyclohexen-1-yl)-1-penten-4-yn-3-ol (XV) by following process.

Approximately 50 mg PdIn alloy catalyst obtained in Embodiment 1 was added to a 50 mL autoclave. Approximately 10 mmol 3-methyl-1-(2,6,6-trimethyl-1-cyclohexen-1-yl)-1-penten-4-yn-3-ol (XV) and about 5 mL ethanol were added. The reaction was taken under a hydrogen pressure of 1 MPa, a reaction temperature of about 30 degree centigrade and reaction time of about 2 hours. A conversion of 3-methyl-1-(2,6,6-trimethyl-1-cyclohexen-1-yl)-1-penten-4-yn-3-ol (XV) was about 100%, and a selectivity of 3-methyl-1-(2,6,6-trimethyl-1-cyclohexen-1-yl)-1,4-pentadien-3-ol (XVI)) was about 98%.

Embodiment 11

The PdIn alloy catalyst catalyzes a selective hydrogenation of 3,6-dimethyl-8-(2,6,6-trimethyl-1-cyclohexen-1-yl)-2,7-octadien-4-yne-1 (XVII) by following process.

Approximately 50 mg PdIn alloy catalyst obtained in Embodiment 1 was added to a 50 mL autoclave. Approximately 10 mmol 3,6-Dimethyl-8-(2,6,6-trimethyl-1-cyclohexen-1-yl)-2,7-octadien-4-yne-1,6-diol (XVII) and about 5 mL ethanol were added. The reaction was taken under a hydrogen pressure of about 1 MPa, a reaction temperature of about 30 degree centigrade and reaction time of about 2 hours. A conversion of 3,6-Dimethyl-8-(2,6,6-trimethyl-1-cyclohexen-1-yl)-2,7-octadien-4-yne-1,6-diol (XVII) was about 100%, and a selectivity of 3,6-dimethyl-8-(2,6,6-trimethyl-1-cyclohexen-1-yl)-2,4,7-octanetriene-1,6-diol (XVIII) was about 98%.

Embodiment 12

The PdIn alloy catalyst catalyzes an application performance of the selective hydrogenation of 2-methyl-3-butyn-2-ol (I) by following process.

Approximately 50 mg PdIn alloy catalyst obtained in Embodiment 1 was added to a 50 mL autoclave. Approximately 20 mmol 2-methyl-3-butyn-2-ol (I) and about 5 mL ethanol were added. The reaction was taken under a hydrogen pressure of about 1 MPa, a reaction temperature of 30 degree centigrade and reaction time of about 2 hours. After the reaction, the PdIn alloy catalyst was taken out by centrifugation, washed three times with ethanol, and dried under vacuum at about 40 degree centigrades. The PdIn alloy catalyst was continued to catalyze the selective hydrogenation of 2-methyl-3-butyn-2-ol (I). The results of the application were shown in Table 1. The result was the performance of the PdIn alloy catalyst was stable, and the activity and selectivity of the PdIn alloy catalyst was maintained after about 15 times of application.

TABLE 1

| Times | Conversion of 2-methyl-3-butyn-2-ol (I) (%) | Selectivity of 2-methyl-3-buten-2-ol (II) (%) | Hydrogenation selectivity (%) | Raw material selectivity (%) |
|---|---|---|---|---|
| 1 | 100 | 99 | <1 | <1 |
| 3 | 100 | 99 | <1 | <1 |
| 6 | 100 | 99 | <1 | <1 |
| 9 | 100 | 99 | <1 | <1 |
| 12 | 100 | 99 | <1 | <1 |
| 15 | 100 | 99 | <1 | <1 |
| 20 | 100 | 99 | <1 | <1 |
| 25 | 100 | 99 | <1 | <1 |
| 30 | 100 | 99 | <1 | <1 |
| 35 | 100 | 99 | <1 | <1 |
| 40 | 100 | 99 | <1 | <1 |
| 45 | 100 | 99 | <1 | <1 |
| 50 | 100 | 99 | <1 | <1 |
| 55 | 100 | 99 | <1 | <1 |
| 60 | 99 | 99 | <1 | <1 |

The technical features of the above-described embodiments may be combined in any combination. For the sake of brevity of description, all possible combinations of the technical features in the above embodiments are not described. However, as long as there is no contradiction between the combinations of these technical features, all should be considered as within the scope of this disclosure.

The above-described embodiments are merely illustrative of several embodiments of the present disclosure, and the description thereof is relatively specific and detailed, but is not to be construed as limiting the scope of the disclosure. It should be noted that a number of variations and modifications may be made by those skilled in the art without departing from the spirit and scope of the disclosure. Therefore, the scope of the disclosure should be determined by the appended claims.

We claim:

1. A PdIn alloy catalyst comprising a carrier and Pd metal particles supported by the carrier, wherein the carrier is a nitrogen-doped porous carbon composite material having a plurality of passages, the Pd metal particles are distributed in the plurality of passages, the nitrogen-doped porous carbon composite material comprises a nitrogen-doped porous carbon material, a plurality of indium oxide particles, and In metal particles, the In metal particles are $In^0$ in a metallic state and partially exposed through the plurality of passages, the plurality of indium oxide particles are uniformly distributed in the nitrogen-doped porous carbon material, and In atoms of the In metal particles migrated to surfaces of Pd particles selectively occupy edge and corner positions of metal lattice of the Pd metal particles.

2. The PdIn alloy catalyst of claim 1, wherein the Pd metal particles have a dispersity of 70% to 95% in the nitrogen-doped porous carbon composite material.

3. The PdIn alloy catalyst of claim 1, wherein a weight percentage of the Pd metal particles in the PdIn alloy catalyst is in a range of 0.1% to 10%, a weight percentage of a sum of the plurality of indium oxide particles and the In metal particles in the PdIn alloy catalyst is in a range of 2% to 30%, a weight percentage of the nitrogen-doped porous carbon composite material in the PdIn alloy catalyst is in a range of 60% to 97.9%, and a weight percentage of nitrogen element in the nitrogen-doped porous carbon composite material is in a range of 0.5% to 15%.

4. The PdIn alloy catalyst of claim 1, wherein the PdIn alloy catalyst is manufactured by:
   providing the nitrogen-doped porous carbon composite material having the plurality of passages, wherein the nitrogen-doped porous carbon composite material comprises the nitrogen-doped porous carbon material and the plurality of indium oxide particles, the plurality of indium oxide particles are uniformly distributed in the nitrogen-doped porous carbon material, and a part of the plurality of indium oxide particles are exposed through the plurality of passages;
   immersing the nitrogen-doped porous carbon composite material in a Pd metal precursor solution;
   treating the nitrogen-doped porous carbon composite material by a first calcination, to convert a Pd metal precursor in the Pd metal precursor solution into Pd metal particles, which are distributed in the plurality of passages; and
   undergoing a hydrogen reduction on the nitrogen-doped porous carbon composite material, wherein in a process of hydrogen reduction, the part of the plurality of indium oxide particles exposed through the plurality of passages are reduced to the In metal particles, and In atoms of the In metal particles migrated to surfaces of Pd particles selectively occupy edge and corner positions of metal lattice of the Pd metal particles, in order to combine with the Pd metal particles.

5. The PdIn alloy catalyst of claim 4, wherein the nitrogen-doped porous carbon composite material is prepared by:
   dissolving an indium nitrate in water to obtain a premix;
   sequentially adding a nitrogen-containing biomass and a pore-forming agent to the premix, such that the indium nitrate reacts with the pore-forming agent to obtain a mixture containing a metal precipitate, wherein the pore-forming agent is at least one selected from a group of ammonium bicarbonate, ammonium carbonate, ammonium oxalate, ammonium hydrogen oxalate, and oxalic acid, a molar ratio of the indium nitrate to the pore-forming agent is 1:1 to 1:20; and
   treating the mixture by a second calcination at 500 degree centigrades to 1200 degree centigrades under an inert atmosphere to obtain the nitrogen-doped porous carbon composite material having the plurality of passages.

6. The PdIn alloy catalyst of claim 4, wherein the Pd metal precursor in the Pd metal precursor solution is at least one of $PdCl_2$, $H_2PdCl_4$, $Pd(NO_3)_2$, and $Pd(NH_3)4(NO_3)_2$.

7. The PdIn alloy catalyst of claim 4, wherein in the first calcination, a calcination temperature is in a range of 200 degree centigrades to 500 degree centigrades, a heating rate is in a range of 1 degree centigrade per minute to 20 degree centigrades per minute, the time is in a range of 1 minute to 240 minutes; in the hydrogen reduction, a reduction temperature is in a range of 50 degree centigrades to 500 degree centigrades, a heating rate is in a range of 1 degree centigrade per minute to 20 degree centigrades per minute, the time is in a range of 1 minute to 360 minutes, and a flow rate of hydrogen gas is in a range of 20 milliliters per minute to 200 milliliters per minute.

8. The PdIn alloy catalyst of claim 5, wherein the nitrogen-containing biomass is at least one of bamboo, chitin, carboxymethyl chitin, chitosan, carboxymethyl chitosan, and glucosamine hydrochloride.

9. The PdIn alloy catalyst of claim 1, wherein the specific surface area of the PdIn alloy catalyst is about 113.7 $m^2g^{-1}$.

\* \* \* \* \*

UNITED STATES PATENT AND TRADEMARK OFFICE
CERTIFICATE OF CORRECTION

PATENT NO. : 10,737,250 B2
APPLICATION NO. : 16/558125
DATED : August 11, 2020
INVENTOR(S) : Yong Wang et al.

Page 1 of 1

It is certified that error appears in the above-identified patent and that said Letters Patent is hereby corrected as shown below:

On the Title Page

Item (72) Inventors should read:
Yong WANG, Hangzhou (CN); Xiao MA, Weifang (CN); Lili YU, Shaoxing (CN); Zhe WANG, Hangzhou (CN); Shanjun MAO, Hangzhou (CN); Jianqing Li, Weifang (CN); Gang CHEN, Hangzhou (CN); Haoran Li, Hangzhou (CN); Zhirong CHEN, Hangzhou (CN)

Signed and Sealed this
Eighth Day of December, 2020

Andrei Iancu
*Director of the United States Patent and Trademark Office*